United States Patent [19]

Barta et al.

[11] 4,281,653
[45] Aug. 4, 1981

[54] COMBINED AMPULE-ONEWAY INJECTION SYRINGE

[75] Inventors: Helmut Barta; Walter Simonich, both of Vienna, Austria

[73] Assignee: Immuno Aktiengesellschaft für Chemisch-Medizinische Produkte, Vienna, Austria

[21] Appl. No.: 82,856

[22] Filed: Oct. 9, 1979

[30] Foreign Application Priority Data

Oct. 16, 1978 [AT] Austria ................................. 7409/78

[51] Int. Cl.³ .............................................. A61M 5/00
[52] U.S. Cl. ................................................ 128/218 D
[58] Field of Search ........... 128/218 D, 218 P, 218 R, 128/215, 216, 221

[56] References Cited

U.S. PATENT DOCUMENTS

| | | | |
|---|---|---|---|
| 1,712,070 | 5/1929 | Cressler | 128/218 D |
| 3,026,872 | 3/1962 | Prater, Jr. | 128/218 P |

Primary Examiner—John D. Yasko
Attorney, Agent, or Firm—Brumbaugh, Graves, Donohue & Raymond

[57] ABSTRACT

A combined ampule-oneway injection syringe comprises a glass syringe body whose inner wall has been treated with a lubricant at a high temperature. One end of the body is permanently closed by a piston after a medicament has been located therein. The needle-side part of the syringe body is designed as a syringe cone having a peripheral annular groove. A connection piece including an inwardly directed nose-shaped part is undetachably engaged in the groove with clamping prior to the filling of the syringe body with medicament. A protecting cap is also located over the needle-carrying connection piece.

4 Claims, 3 Drawing Figures

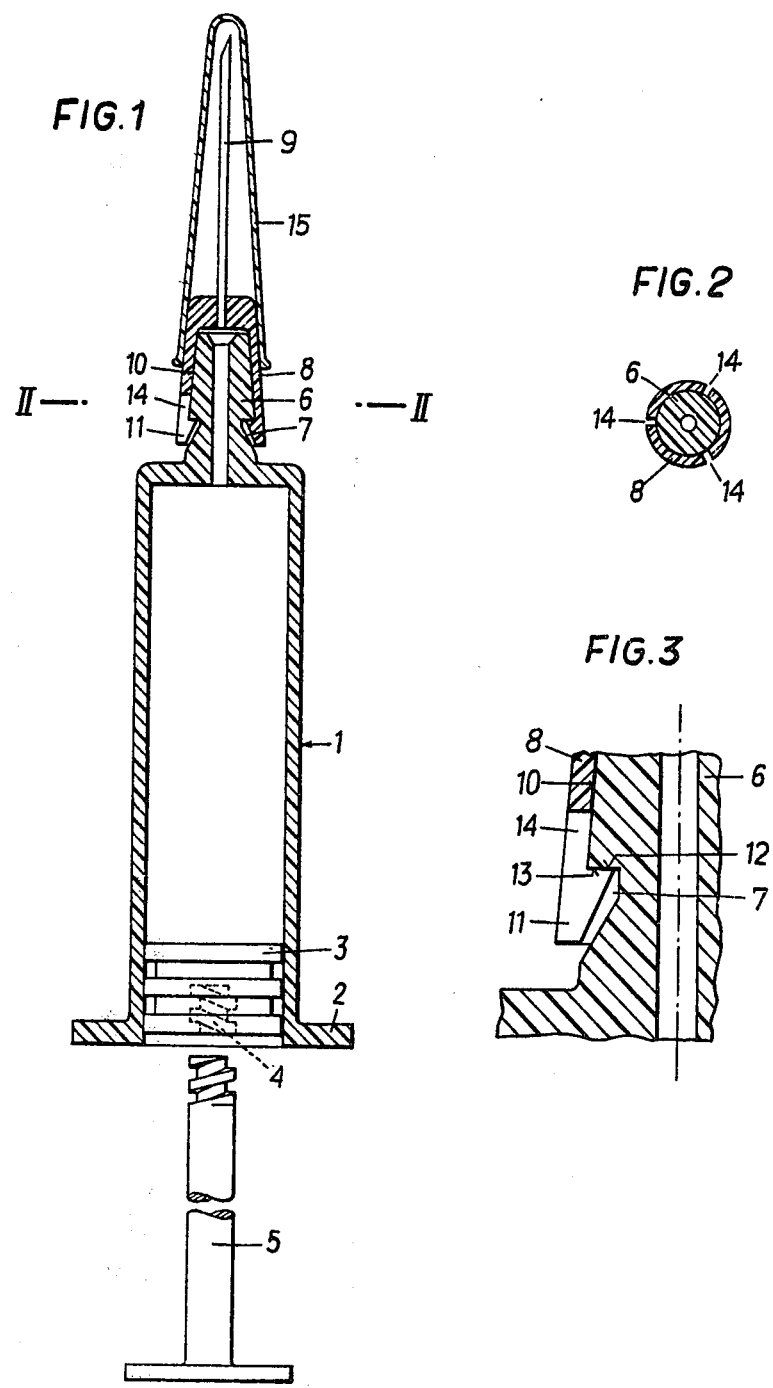

COMBINED AMPULE-ONEWAY INJECTION SYRINGE

BACKGROUND OF THE INVENTION

The invention relates to a combined ampule-oneway injection syringe comprising a syringe body destined for accommodating the injection liquid, and a needle-carrying connection piece.

Injection syringes of this kind have been offered separately as a storage container containing medicament and as a pertaining antiseptically packed connection piece carrying the needle. The connection piece with the needle is slipped on the syringe cone by the physician prior to the application. This manipulation bears the risk of bacterial contamination, thus defeating the object, which would be obtainable with oneway injection syringes in which the connection between the syringe body and the connection piece having the injection needle is undetachable, of assuring that, after filling of the syringe body with the medicament, sterile conditions are safeguarded until the application of the medicament.

Ampule-oneway injection syringes which include injection needles that are undetachably fastened thereto and whose syringe bodies contain the medicament and are closed by a movable piston, are well known. With these, the injection needle is glued into the syringe cone by a glue having a polyester base. These ampule-oneway injection syringes, however, have the disadvantage that they are difficult to produce because the inner wall of the syringe body has to be treated with a lubricant, advantageously with silicone, which is evaporated onto the wall at approximately 300° C. The polyester glue, however, cannot withstand these high temperatures without changing its color or being destroyed. Also when inversely operating, i.e. introducing the lubricant first and gluing on the needle afterwards, unsolvable difficulties will frequently occur, since a silicone-treated surface evidently will not accept a glue. The known ampule-oneway injection syringes of this kind have the further disadvantage that it is necessary to keep an extensive stock since every needle dimension (length and diameter) and every syringe body has to be produced as a production unit; it therefore is not possible to assemble a desired, separately produced needle of a particular dimension with a desired, separately produced syringe body prior to filling the body with the medicament.

Moreover, ampule-oneway injection syringes have also been known to have a double needle undetachably fastened to one end and a glass body containing the medicament, which glass body is insertable into the syringe body. The glass body comprises a rubber closure with a welt at the side of the needle and is closed by a displaceable piston at the other side. Injection syringes of this kind are accordingly expensive.

SUMMARY OF THE INVENTION

The invention aims at avoiding the disadvantages and difficulties described and has as its object to provide ampule-oneway injection syringes with which it is possible to undetachably connect, prior to filling with the medicament, separately produced syringe bodies with separately produced connection pieces having selective needle dimensions, thus ensuring sterile original fillings and preventing any risk of impurities prior to the application of the medicament. Furthermore, the invention aims at reducing and simplifying stock-keeping procedures.

This object is achieved according to the invention with an ampule-oneway injection syringe of the initially-defined kind by a combination of the following characteristic features, (a) the syringe body comprises a glass body which is open at one end and, after filling with a medicament, is permanently closeable by a piston, (b) the inner wall of the glass body is treated with a lubricant at a high temperature, advantageously it is silicone-treated at 300° C., (c) the part of the syringe body on the end adapted to receive the needle, is designed as a syringe cone having a peripheral annular groove, (d) the connection piece comprises an inwardly directed nose-shaped part engaging the peripheral groove of the syringe cone with a clamping closure, and (e) a covering cap is put on above the connection piece carrying the needle.

Advantageously, the connection piece is produced of synthetic material and comprises longitudinal slots in the region of the inwardly directed nose-shaped parts in order to effect a resilient clamping closure.

According to a preferred embodiment, the contact faces of the inwardly directed nose-shaped part and the peripheral groove extend perpendicular to the axis of the injection syringe and the moving direction of the piston, respectively.

After having assembled the syringe body and the connection piece, the contact faces of the inwardly directed nose-shaped part and the peripheral groove lie on each other without play and so as to be undetachable.

According to the invention, it is possible to combine any desired syringe body with any desired connection piece and a needle of any desired dimensions.

With injection syringes of a conventional type, such as for instance according to Swiss patent No. 585,560, it is known per se to use a connection piece which comprises an inwardly directed nose-shaped part that engages with a clamping closure in a groove of the pipe-section-shaped syringe body; however, these syringes cannot be utilized as accommodation and storage containers for medicaments and are thus not suitable to meet the high demands for sterile application.

BRIEF DESCRIPTON OF THE DRAWINGS

The subject matter of the invention will now be explained in more detail with reference to the accompanying drawing, wherein:

FIG. 1 is a longitudinal section of a syringe according to the invention;

FIG. 2 is a cross section through line II—II of FIG. 1; and

FIG. 3 represents a detail on an enlarged scale.

DESCRIPTION OF AN ILLUSTRATIVE EMBODIMENT

In the drawing a cylindrical syringe body 1 has a flange 2 at its lower end. The syringe body is closeable at this end by a piston 3 having an inner thread 4 into which an actuating rod 5 can be screwed. At the upper end the syringe body ends in a syringe cone 6 which, according to the invention, comprises a peripheral groove 7. Onto the syringe cone, a connection piece 8 carrying a needle 9 and advantageously produced of synthetic material can be put, which connection piece has the same conicity as the syringe cone, so that a conical sealing face, which is denoted by 10, will be present between these two parts. The connection piece, at its lower rim, comprises an inwardly directed nose 11 which backs the upper wall 12 of the groove 7, engaging into the same with a clamping closure. The contact face 13 of the inwardly directed nose 11 in this way comes to lie at the upper wall or contact face 12 of the syringe cone 6 without play. These contact faces extend perpendicular to the axis of the injection syringe and the moving direction of the piston, respectively. Thus, the connection piece with the injection needle is undetachably connected with the syringe body.

Advantageously, assembly of the connection piece and the syringe cone is simplified in that the lower part of the connection piece comprises longitudinal slots 14, thus giving a certain resilience to the lower part of the connection piece. The inwardly directed nose-shaped parts can elastically and resiliently slide over the conical sealing face 10 until they snap into groove 7. A protecting cap 15 is put over the needle 9 and the connection piece.

What we claim is:

1. A combined ampule-oneway injection syringe comprising in combination
    a syringe body made of glass and having a first end and a second end, said first end terminating in a syringe cone provided with a peripheral annular groove, the inner wall of said syringe body being treated with a lubricant,
    a needle-carrying connection piece including an inwardly directed nose-shaped part engaging in said peripheral annular groove of said syringe cone by clamping closure, such that said connection piece is undetachably connected with said syringe cone prior to the filling of the syringe body with medicament,
    a piston for permanently closing said second end of said syringe body after said body has been filled with medicament to be stored for administration, and
    a protecting cap located over said needle-carrying connection piece.

2. A combined ampule-oneway injection syringe as set forth in claim 1, wherein said glass body has been treated, at its inner wall, with silicone at 300° C.

3. A combined ampule-oneway injection syringe as set forth in claim 1, wherein said connection piece includes longitudinal slots provided in the region of said inwardly directed nose-shaped parts.

4. A combined ampule-oneway injection syringe as set forth in claim 1, 2 or 3, wherein said connection piece has a cone shape corresponding to said syringe cone so that a conical sealing face is present therebetween and wherein a first contact face is formed on said peripheral groove and a second contact face is formed on said inwardly directed nose-shaped part, said first and said second contact faces extending perpendicular to the axis of said injection syringe and to the moving direction of said piston.

* * * * *